United States Patent … US 11,830,308 B1
Warnick et al. … Date of Patent: Nov. 28, 2023

(54) ACCESS CONTROL SYSTEM FOR MAINTAINING ACCEPTABLE HEALTH AND SAFETY STANDARDS IN GROUP SETTINGS

(71) Applicant: UIPCO, LLC, San Antonio, TX (US)

(72) Inventors: Mark Paxman Warnick, San Antonio, TX (US); Will Kerns Maney, Jr., San Antonio, TX (US); Phillip E. Marks, San Antonio, TX (US); David Jason Anderson James, San Antonio, TX (US); Elena Marie Carrasco, Converse, TX (US); Quian Antony Jones, San Antonio, TX (US); Sumita T. Jonak, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 367 days.

(21) Appl. No.: 17/164,120

(22) Filed: Feb. 1, 2021

Related U.S. Application Data

(60) Provisional application No. 63/106,988, filed on Oct. 29, 2020.

(51) Int. Cl.
| | |
|---|---|
| G07C 9/27 | (2020.01) |
| G16H 50/30 | (2018.01) |
| G16H 40/67 | (2018.01) |
| G06K 19/06 | (2006.01) |
| G16H 10/65 | (2018.01) |
| G07C 9/25 | (2020.01) |
| G07C 9/29 | (2020.01) |
| G06K 7/14 | (2006.01) |

(Continued)

(52) U.S. Cl.
CPC ............ *G07C 9/27* (2020.01); *A61B 5/7275* (2013.01); *G06K 7/1417* (2013.01); *G06K 19/06037* (2013.01); *G06K 19/06112* (2013.01); *G06V 40/168* (2022.01); *G07C 9/25* (2020.01); *G07C 9/29* (2020.01); *G10L 25/66* (2013.01); *G16H 10/40* (2018.01); *G16H 10/65* (2018.01); *G16H 40/67* (2018.01); *G16H 50/30* (2018.01); *A61B 5/14551* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 11,151,820 B1* | 10/2021 | Klein | G06Q 50/265 |
| 11,504,011 B1* | 11/2022 | Jain | G16H 10/20 |

(Continued)

*Primary Examiner* — Kristy A Haupt
(74) *Attorney, Agent, or Firm* — Plumsea Law Group, LLC

(57) ABSTRACT

A user device may obtain access control data which is derived based on a test result or score of a test for assessing a risk of a user of having or developing a contagious illness. The access control data may be communicated from the user device to an access control system in response to a reading of the user device by the access control system. The access control system may permit or deny entry of the user into an area based on the access control data. In some aspects, the user device is an identity (ID) or access badge. In other aspects, the user device is a mobile user device having one or more illness risk factor assessment functions, where the test result or score is obtained based on resulting data from executing the one or more illness risk factor assessment functions.

20 Claims, 11 Drawing Sheets

(51) Int. Cl.
   *G10L 25/66* (2013.01)
   *A61B 5/00* (2006.01)
   *G16H 10/40* (2018.01)
   *G06V 40/16* (2022.01)
   *A61B 5/1455* (2006.01)

(56) References Cited

U.S. PATENT DOCUMENTS

2020/0279464 A1* 9/2020 Llewelyn ................ G06F 3/147
2021/0358068 A1* 11/2021 Boszczyk ............ G06Q 50/265

\* cited by examiner

ACCESS CONTROL SYSTEM FOR MAINTAINING ACCEPTABLE HEALTH AND SAFETY STANDARDS IN GROUP SETTINGS

CROSS-REFERENCE TO RELATED APPLICATION(S)

This application claims the benefit of U.S. Provisional Patent Application No. 63/106,988, filed Oct. 29, 2020, and titled "Access Control System for Maintaining Acceptable Health and Safety Standards in Group Settings", the disclosure of which application is incorporated by reference herein in its entirety.

TECHNICAL FIELD

The present disclosure generally relates to access control systems and, in particular, to techniques and mechanisms for access control for maintaining acceptable health and safety standards in group settings.

BACKGROUND

Under occupational safety and health laws, employers and other organizations have duties to maintain safe operating environments. Those duties may include taking reasonable measures to prevent the spread of disease. For example, in order to prevent the outbreak of contagious diseases, organizations should take basic measures such as making tissues and antibacterial soap available. Encouraging hand washing, disinfecting, offering flu shots, and urging people to get immunizations are also good practices. Of course, other group settings may have the same or similar concerns and needs.

One notable concern is a recent virus that was designated as severe acute respiratory syndrome coronavirus 2 (SARS-CoV-2) defined to be the causal agent of Coronavirus Disease 2019 (COVID-19). Despite attempts to contain the disease, the virus has spread globally and COVID-19 was declared a pandemic by the World Health Organization (WHO) in March 2020.

There is a need in the art for techniques and mechanisms for maintaining acceptable health and safety standards in group settings that address the problems discussed above, as well as related issues.

SUMMARY

Various techniques and mechanisms for access control for maintaining acceptable health and safety standards in group settings are described herein.

In one aspect, a user device may obtain access control data which is derived based on a test result or score of a test for assessing a risk of a user of having or developing a contagious illness. The access control data may be communicated from the user device to an access control system in response to a reading of the user device by the access control system. The access control system may permit or deny entry of the user into an area based on the access control data. In some embodiments, the user device may derive, determine, or retrieve the access control data based on the test result or score of the test. In one example, the user device may be an identification (ID) or access badge or device associated with the user. In another example, the user device may be a mobile user device associated with the user.

In another aspect, a mobile user device may include one or more processors, a user interface, and a radio transceiver configured to connect to a mobile network for communications. The one or more processors may be configured to obtain access control data which is derived based on a test result or score of a test for assessing a risk of a user of having or developing a contagious illness. The one or more processors may be further configured to communicate the access control data to an access control system in response to a reading of the mobile user device by the access control system, for causing the access control system to permit or deny entry of the user into an area. In some embodiments, the one or more processors of the mobile user device may be configured to derive, determine, or retrieve the access control data based on the test result or score of the test.

In one example using a mobile user device, the access control data may be derived based on a test result or score of a test which is or includes a viral test or an antibody test. The viral test or the antibody test may be processed at a health care laboratory based on a sample of the user. Here, resulting data of the viral test or the antibody test may be retrieved by the mobile user device via a health care server portal.

In another example using a mobile user device, the access control data may be derived based on a test result or score of a test which includes one or more illness risk factor assessment functions executed at the mobile user device. The one or more illness risk factor assessment functions may include a temperature detection function which is based on a temperature of the user; an image-based symptom recognition function which is based on facial characteristics of the user, with a camera of the mobile user device; an audio-based symptom recognition function which is based on qualities of voice, nasal, or congestion of the user, with an audio recorder of the mobile user device; or a pulse oximeter function based on blood oxygenation.

In yet another aspect, a controller of an access control system may obtain access control data based on a reading of a user device of a user. The access control data may be derived based on a test result or score of a test for assessing a risk of the user of having or developing a contagious illness. The controller may communicate a signal to an entry mechanism of the access control system, for permitting or denying entry of the user into an area based on the access control data. In some embodiments, the access control system includes a reader which is configured to read the user device which is or includes an ID or access badge or device associated with the user. In other embodiments, the access control system includes a reader which is configured to read the user device which is or includes a mobile user device associated with the user. In some embodiments, the access control system may derive, determine, or retrieve the access control data based on the test result or score of the test for the user. In other embodiments, the access control system may retrieve the access control data based on an identifier of the user of the user device.

Other techniques, mechanisms, features, and advantages of the disclosure will be, or will become, apparent to one of ordinary skill in the art upon examination of the following figures and detailed description. It is intended that all such additional techniques, mechanisms, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

Figure 1:
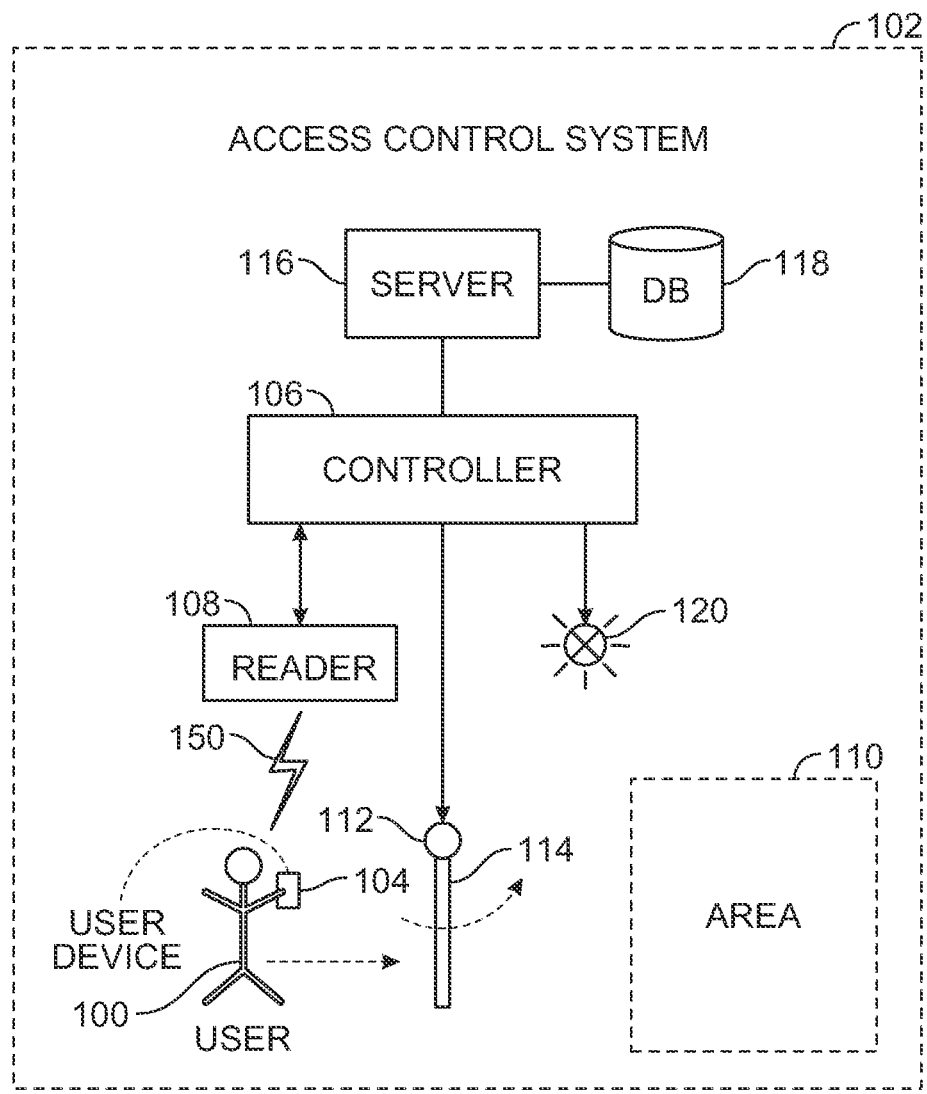
FIG. 1 is a schematic block diagram of an access control system for access control to an area for maintaining acceptable health and safety standards in group settings according to some embodiments.

As described in the Background section, under occupational safety and health laws, employers and other organizations may have duties to maintain safe operating environments. Those duties can include taking reasonable measures to prevent the spread of disease. For example, in order to prevent the outbreak of contagious diseases, organizations should take basic measures such as making tissues and antibacterial soap available. Encouraging hand washing, disinfecting, offering flu shots, and urging people to get immunizations are also good practices. Of course, other group settings may have the same or similar concerns and needs.

In late December 2019, several cases of pneumonia of unknown origin were reported from China, which in early January 2020 were announced to be caused by a novel coronavirus. This virus was later designated as severe acute respiratory syndrome coronavirus 2 (SARS-CoV-2) defined to be the causal agent of Coronavirus Disease 2019 (COVID-19). Despite attempts to contain the disease, the virus has spread globally and COVID-19 was declared a pandemic by the World Health Organization (WHO) in March 2020.

Various techniques and mechanisms for access control for maintaining acceptable health and safety standards in group settings are described herein. In some embodiments, a controller of an access control system may obtain access control data based on a reading of a user device of a user. The access control data may be derived based on a test result or score of a test for assessing a risk of the user of having or developing a contagious illness (e.g. COVID-19). The controller may communicate a signal to an entry mechanism of the access control system, for permitting or denying entry of the user into an area based on the access control data.

In other embodiments, a user device of a user may obtain access control data which is derived based on a test result or score of a test for assessing a risk of the user of having or developing a contagious illness (e.g. COVID-19). The access control data may be communicated from the user device to an access control system in response to a reading of the user device by the access control system. The access control system may permit or deny entry of the user into an area based on the access control data. In some embodiments, the user device may derive, determine, or retrieve the access control data based on the test result or score of the test. Accordingly, access control for maintaining acceptable health and safety standards in group settings is provided.

In some embodiments, the user device may be an identification (ID) or access badge or other device associated with the user. In an example embodiment, the user device may be a mobile user device (e.g. a smartphone or a tablet computer). Using a mobile user device, the access control data may be derived based on a test result or score of a test which is or includes a viral test or an antibody test. Also using a mobile user device, the access control data may be derived based on a test result or score of a test which includes one or more illness risk factor assessment functions executed at the mobile user device.

As employers and other organizations may have duties to maintain safe operating environments, which can include taking reasonable measures to prevent the spread of disease, the techniques and mechanisms of the present disclosure can provide additional assurances of health and safety in group settings. In addition, the techniques and mechanisms of the present disclosure may leverage existing technology to minimize changes to existing devices, systems, and network architectures. Also, as access control data may be derived based on test results or scores of tests of users, and not include the actual test results or scores of the tests of the users, compliance with Health Insurance Portability and Accountability Act (HIPAA) and/or other regulatory standards, policies, and practices. Use of any sensitive test results or scores of users in the network or system may be immediately discarded (e.g. deleted or cleared) after derivation of access control data.

To better illustrate in relation to the figures, FIG. 1 is a schematic block diagram of an access control system 102 for access control to an area 110 for maintaining acceptable health and safety standards in group settings according to some embodiments. More particularly, access control system 102 is configured for access control of a user 100 into area 110 based on a reading of a user device 104 of user 100. Access control system 102 may be configured to obtain access control data based on or in response to the reading of user device 104, where the access control data is derived based on a test result or score of a test for assessing a risk of user 100 of having or developing a contagious illness.

As illustrated in FIG. 1, access control system 102 may include a controller 106, a reader 108, and an entry mechanism 114. Reader 108 may be configured to read data from user device 104. The data that are read from user device 104 of user 100 may be or include identity data of an identity of user 100, access control data for access control, or both. The type of reader 108 will depend on the system and the implementation of user device 104. Different types and varieties of devices are described herein and later in relation to FIGS. 8-9. In one example, reader 108 may be configured to read user device 104 which is an identification (ID) or access badge or other device according to its underlying technology. As another example, reader 108 may be configured to read user device 104 which is a mobile user device (e.g. a smartphone or a tablet computer) according to its underlying technology.

Entry mechanism 114 may be or include a mechanism for entry or access, which may include a door, a turnstile, a gate, an elevator, a parking gate, or other similar mechanisms. Controller 106 may be configured to communicate a signal to entry mechanism 114 for opening or closing of (or unlocking or maintaining locking of) entry mechanism 114 to permit or deny access of user 100 into area 110 based on access control data. In particular, controller 106 may communicate the signal to a switch 112 (e.g. a relay, a latch, electromechanical device, etc.) for opening or closing of (or unlocking or maintaining locking of) entry mechanism 114 to permit or deny access.

Access control system 102 may additionally or alternatively include an alert device 120 for permitting or denying access of user 100 into area 110 based on access control data. In one example, alert device 102 may be a lamp or light-emitting diode (LED). In another example, alert device 102 may be an audio device (e.g. a speaker). When permitting access of user 100 into area 110 based on the access control data, controller 106 may be configured to communicate a "permission" signal to alert device 120 (e.g. lighting the lamp "green" and/or audio signaling a positive sound). On the other hand, when denying access of user 100 into area 110 based on the access control data, controller 106 may be configured to communicate a "denial" signal to alert device 120 (e.g. lighting the lamp "red" and/or audio signaling a negative sound or buzz).

Area 110 may be managed by an organization for access control of users to and/or from area 110. The type of organization for access control of the users may depend on the type of group setting associated with area 110. Area 110 may be associated with one of many different types of group settings. Area 110 may be an indoor venue area associated with an indoor venue or an outdoor venue area association with an outdoor venue. Area 110 may be a building space area associated with a building space (a building or one or more rooms within the building). The building space area may be a commercial building space area, an employer building space area, a governmental building space area, or a residential building space area. For example, area 110 may be an area of an airport or an airplane, a shopping mall, a school, a courthouse or courtroom, a theatre, a concert stadium, a sports stadium, a park, or a festival, to name but a few. In addition, area 110 may be an area associated with a border crossing, for example, for entry into a (new) city, a county, a district, a state, a providence, or a country, etc.

In some embodiments, controller 106 may interface with a server 116 having a database 118. In one example, server 116 may be a local server in a private local area network (LAN) or wireless LAN (WLAN) (e.g. based on IEEE 802.11 standards) of the organization that manages entry into area 110. In another, server 116 may be an external server that is external to the private LAN or WLAN of the organization that manages entry into area 110. The external server may be provided for access in a public network (e.g. the Internet) or a different private LAN, as examples. Database 118 could be co-located with server 116 or could be a remote database that is accessible to server 116 over a network. Database 116 may include any kind of storage device, including but not limited magnetic, optical, magneto-optical, and/or memory, including volatile memory and non-volatile memory.

Figure 2:
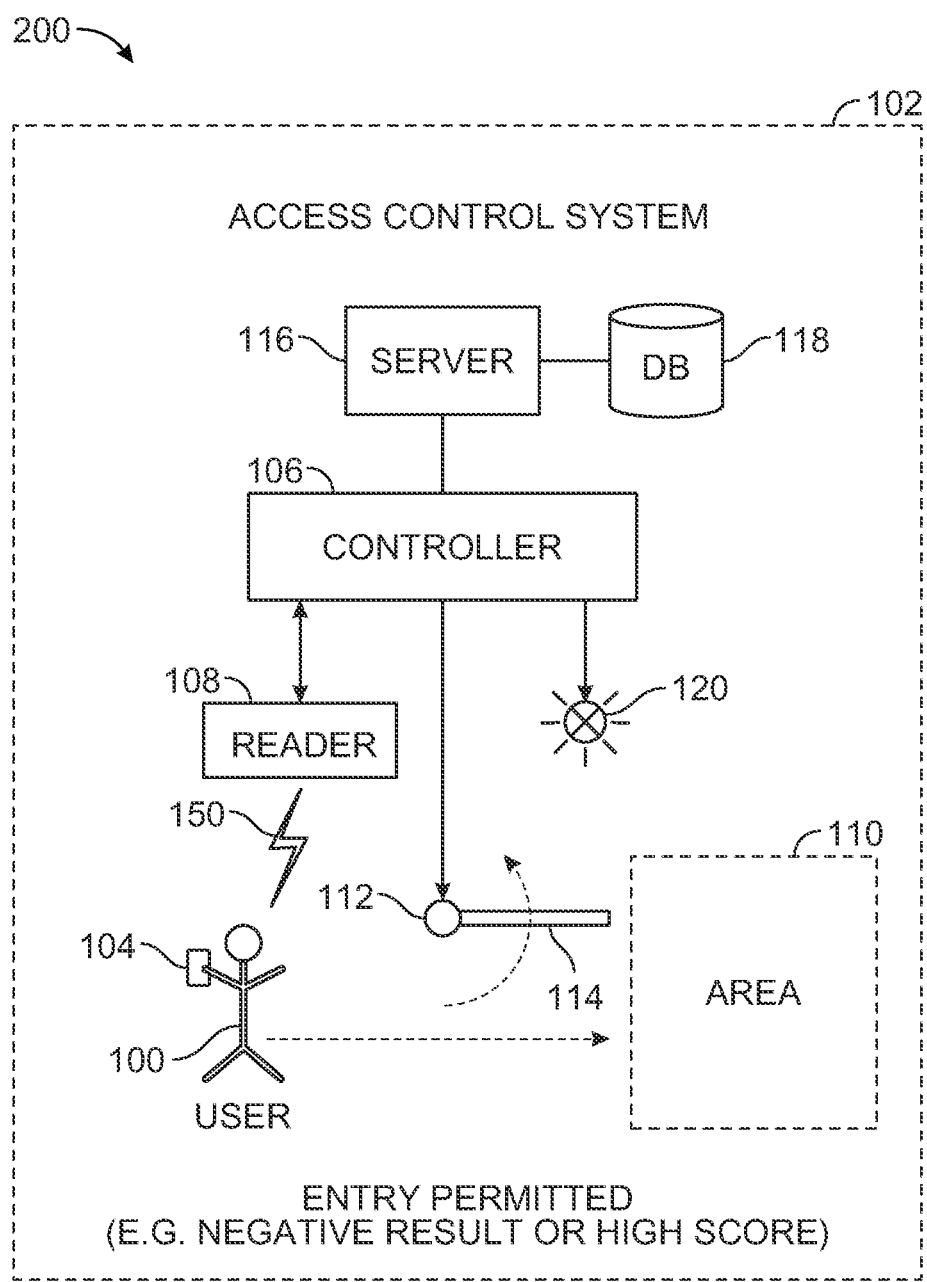
FIG. 2 is the schematic block diagram of the access control system of FIG. 1, illustrating a first example scenario where the access control system permits entry of a user into an area based on a reading of a user device of the user (e.g. a negative result or high score of a test for a contagious illness)

FIG. 2 is the schematic block diagram of access control system 102 of FIG. 1, illustrating a first example scenario 200 where access control system 102 operate to permit entry of user 100 into area 110 based on a reading of user device 104. More specifically, access control system 102 may obtain access control data based on or in response to the reading of user device 104, where the access control data is derived based on a test result or score of a test for assessing a risk of user 100 of having or developing a contagious illness. In first example scenario 200 of FIG. 2, the access control data that is obtained may be derived based on a test result that is negative for the contagious illness, and/or a score that is a high score indicating a low risk for the contagious illness, which permits entry of user 100 into area 110.

Figure 3:
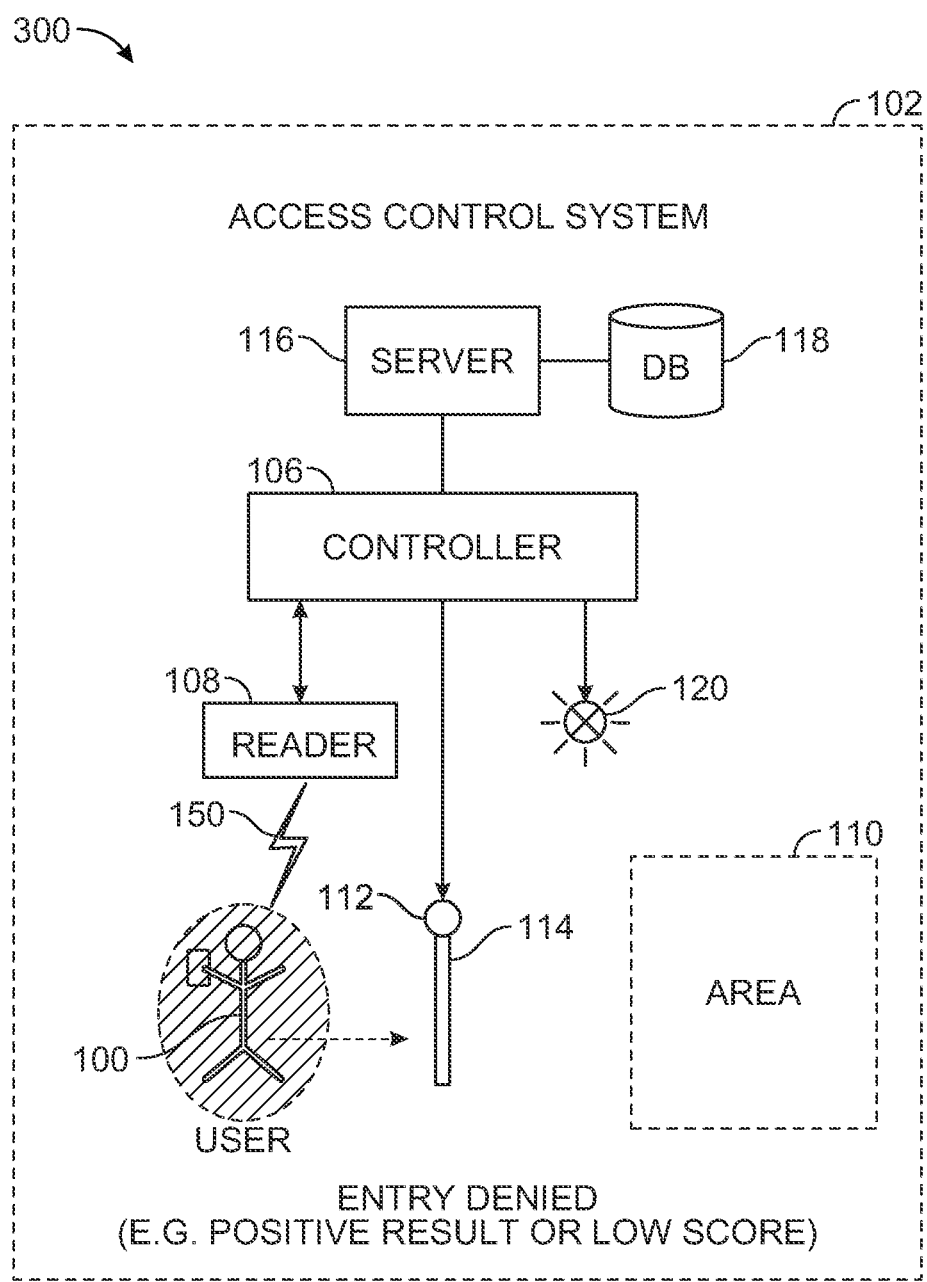
FIG. 3 is the schematic block diagram of the access control system of FIG. 1, illustrating a second example scenario where the access control system denies entry of the user into the area based on a reading of the user device of the user (e.g. a positive result or low score of the test for the contagious illness)

FIG. 3 is the schematic block diagram of access control system 102 of FIG. 1, illustrating a second example scenario 300 where access control system 102 operates to deny entry of user 100 into area 110 based on a reading of user device 104. Again, access control system 102 may obtain access control data based on or in response to a reading of user device 104, where the access control data is derived based on the test result or score of the test for assessing the risk of user 100 of having or developing the contagious illness. In second example scenario 200 of FIG. 2, user 100 has tested positive for the contagious illness, and/or has a low score indicating a high risk of having or developing the contagious illness. The access control data that is obtained may be derived based on the test result that is positive and/or the score that is the low score indicating the high risk, which denies entry of user 100 into area 110.

With this arrangement, as is apparent in relation to FIGS. 1-3, access control system 102 is operative to maintain acceptable health and safety standards in the group setting associated with area 110.

Note that, according to the present disclosure, scores and/or any other resulting data from tests may be fashioned according to the specific techniques utilized and will be functionally dependent on them. For example, lower scores may indicate higher risks and higher scores may indicate lower risks; alternatively, however, lower scores may indicate lower risks and higher scores may indicate higher risks.

Figure 4:
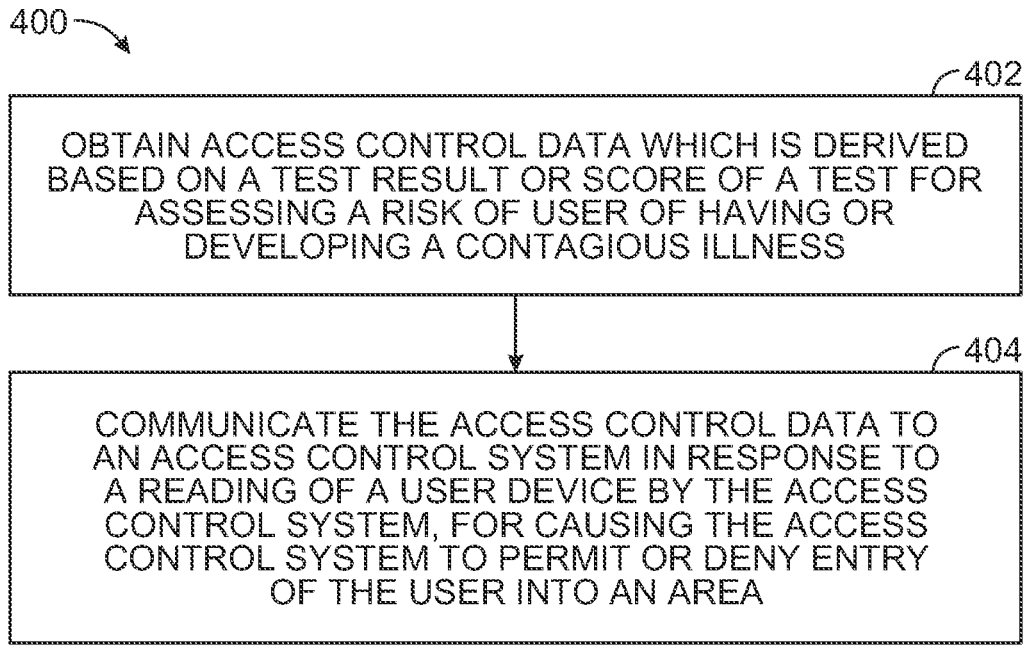
FIG. 4 is a flowchart for describing a method for access control for maintaining acceptable health and safety standards in group settings according to some embodiments, which may be performed by a user device of a user.

FIG. 4 is a flowchart for describing a method 400 for access control for maintaining acceptable health and safety standards in group settings according to some embodiments. Method 400 shown in FIG. 4 may be performed by a user device of a user (e.g. user device 104 of user 100 of FIGS. 1-3). In some embodiments, the user device may be ID or access badge or other device associated with the user. In other embodiments, the user device may be a mobile user device associated with the user. In yet other embodiments, method 400 may be embodied in a computer program product having a non-transitory computer readable medium and instructions stored in the non-transitory computer readable medium, where the instructions are executable by one or more processors of the user device to perform steps of method 400.

In this embodiment, method 400 begins with a step 402. At step 402, the user device may obtain access control data which is derived based on a test result or score of a test for assessing a risk of a user of having or developing a contagious illness. Next, method 400 may proceed to a step 404, where the access control data may be communicated from the user device to an access control system in response to a reading of the user device by the access control system. In response, the access control system may permit or deny entry of the user into an area based on the access control data.

In one example, the access control data may have at least a first indication value and a second indication value. The access control data may be set with the first indication value for permitting entry of the user, based on the test result of the test being a negative test result, or alternatively, based on the score of the test being within a limit set by a threshold value for the user (e.g. a user with a score above the threshold value may be determined to be a low risk and may be permitted entry). The access control data may be set with the second indication value for denying entry of the user, based on the test result of the test being a positive test result, or alternatively, based on the score of the test being outside the limit set by the threshold value for the user (e.g. a user with a score below the threshold value may be determined to be a high risk and may be denied entry).

In some embodiments of method 400, at step 402, the user device may obtain the access control data by setting or determining the access control data, at the user device, based on the test result or score of the test. In one example, the user device may obtain a test result which a negative test result or a score which is within a limit set by a threshold value, and in response, set or determine the access control data to be the first indication value for permitting entry. In a corresponding fashion, the user device may obtain a test result which a positive test result or a score which is outside the limit set by the threshold value, and in response, set or determine the access control data to be the second indication value for denying entry. If the test provides a score (e.g. rather than a positive or negative test result), the user device may compare the score with the threshold value in the setting or determining of the access control data.

In an example embodiment of step 402 of method 400, the user device may be a mobile user device (e.g. a smartphone or a tablet computer) having an application which includes one or more test functions for assessing a risk of a user of having or developing a contagious illness. These test functions may be or include one or more illness risk factor assessment functions. Resulting data from executing the one or more illness risk factor assessment functions at the mobile user device may be used to obtain the test result or score of the test, which is used at step 402.

In other example embodiments of step 402 of method 400, the mobile user device may access resulting data of a test which is a viral test or an antibody test for the user. In some cases, the viral test or the antibody test may be processed at a health care laboratory based on a sample of the user. The access control data may be derived, determined, or retrieved by the mobile user device based on a test result or score of the viral test or the antibody test for the user. For example, the resulting data of the test may be retrieved by the mobile user device via a health care server portal.

Figure 5:
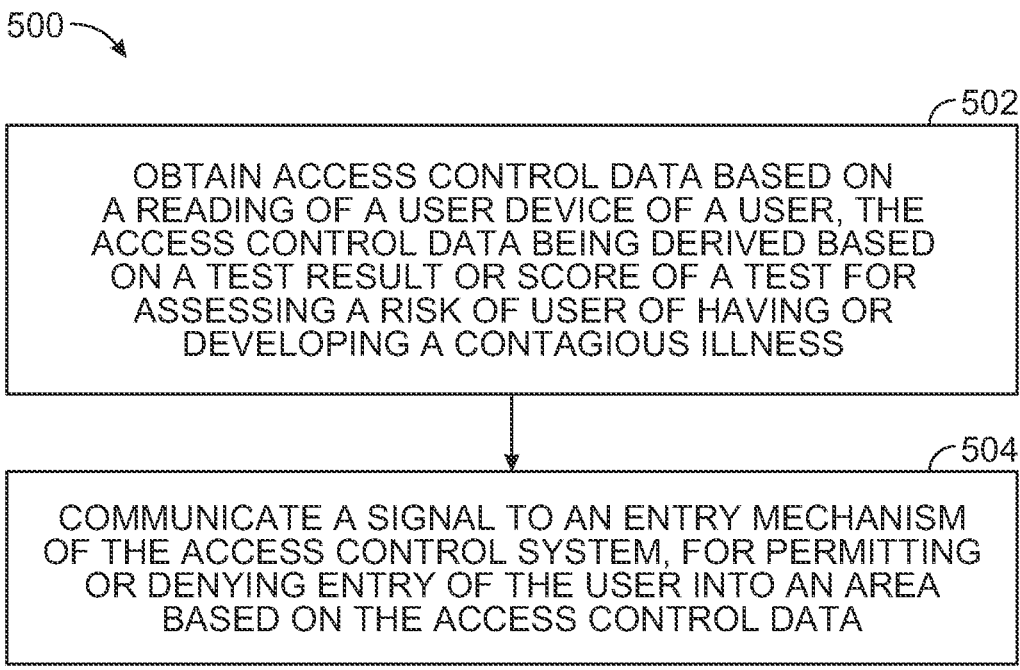
FIG. 5 is a flowchart for describing a method for access control for maintaining acceptable health and safety standards in group settings according to some embodiments, which may be performed by a controller of an access control system.

FIG. 5 is a flowchart for describing a method 500 for access control for maintaining acceptable health and safety standards in group settings according to some embodiments. Method 500 shown in FIG. 5 may be performed by a controller of an access control system (e.g. controller 106 of access control system 102 of FIGS. 1-3). In some embodiments, method 500 may be embodied in a computer program product having a non-transitory computer readable medium and instructions stored in the non-transitory computer readable medium, where the instructions are executable by one or more processors of the controller to perform steps of method 500.

In this embodiment, method 500 begins with a step 502. At step 502, the controller of the access control system may obtain access control data based on a reading of a user device of a user, where the access control data is derived based on a test result or score of a test for assessing a risk of the user of having or developing a contagious illness. Next, method 500 may proceed to a step 504, where the controller of the access control system may communicate a signal to an entry mechanism of the access control system, for permitting or denying entry of the user into an area based on the access control data.

In one example, the access control data may have at least a first indication value and a second indication value. The access control data may be set with the first indication value for permitting entry of the user, based on the test result of the test being a negative test result, or alternatively, based on the score of the test being within a limit set by a threshold value for the user (e.g. a user with a score above the threshold value may be determined to be a low risk and may be permitted entry). The access control data may be set with the second indication value for denying entry of the user, based on the test result of the test being a positive test result, or alternatively, the score of the test being outside the limit set by the threshold value for the user (e.g. a user with a score below the threshold value may be determined to be a high risk and may be denied entry).

In some embodiments of method 500, at step 502, the controller of the access control system may receive the access control data from the user device from the reading of the user device. In some cases, the controller may additionally receive an identifier of the user of the user device together with the access control data.

In other embodiments of method 500, at step 502, the controller of the access control system may receive from the user device the identifier of the user based on the reading of the user device, and subsequently retrieve from a server (e.g. server 116 of FIGS. 1-3) the access control data based on the identifier of the user.

Figure 6:
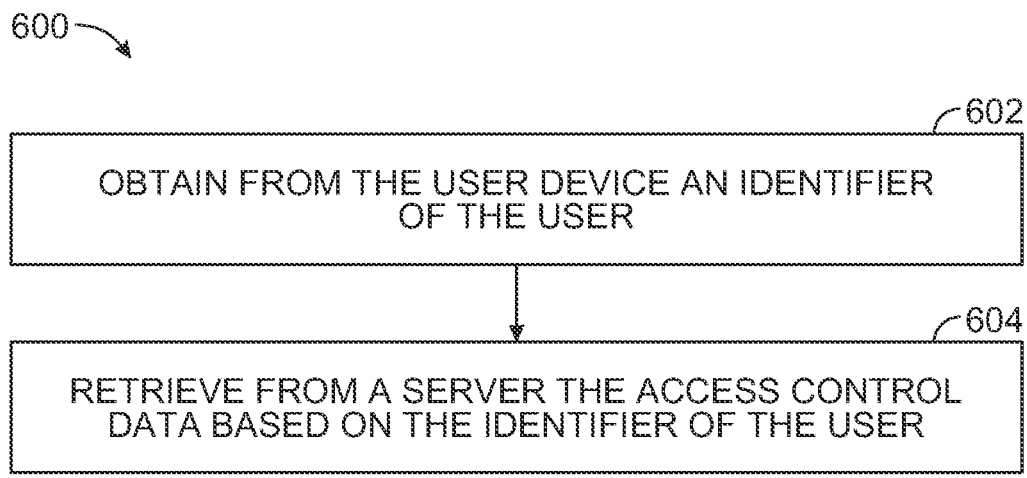
FIG. 6 is a flowchart for describing a method for access control for maintaining acceptable health and safety standards in group settings according to some embodiments, which may be performed by the controller of the access control system and involve retrieving access control data based on an identifier of the user device.

FIG. 6 is a flowchart for describing a method 600 for access control for maintaining acceptable health and safety standards in group settings according to some embodiments. Method 600 shown in FIG. 6 may be performed by a controller (and/or a server) of an access control system (e.g. controller 106 of access control system 102 of FIGS. 1-3). Alternatively, method 600 shown in FIG. 6 may be performed by a server (e.g. server 116 having database 118 of FIGS. 1-3) which may interact with the controller. In some embodiments, method 600 may be embodied in a computer program product having a non-transitory computer readable medium and instructions stored in the non-transitory computer readable medium, where the instructions are executable by one or more processors of the controller/server to perform steps of method 600. For method 600, one or more databases may maintain storage of identifiers of users in association with access control data associated with the user.

In this embodiment, method 600 begins with a step 602. At step 602, the controller/server may obtain or receive, from a user device of a user, an identifier of the user from the reading of the user device. The identifier of the user may be, for example, a user ID associated with the organization that manages entry into the area. Next, method 600 may proceed to a step 604, where the controller/server may retrieve the access control data based on the identifier of the user.

In some cases, data associated with a test result or score may be more sophisticated than data indicating a mere "positive" or "negative" result, and therefore may require a more sophisticated type of processing to determine the appropriate access control data for permitting or denying entry. Accordingly, in some embodiments, data associated with the test result or score may be processed according to one or more policy rules of an organization. The policy rules may be associated with access control according to a predetermined standard. In one example, the test result or score may be processed according to one or more policy rules of an organization (e.g. a business or employer) that manages entry into an area having an access control system. In another example, the test result or score may be processed according to one or more policy rules mandated by a governmental organization associated with health and safety.

Figure 7:
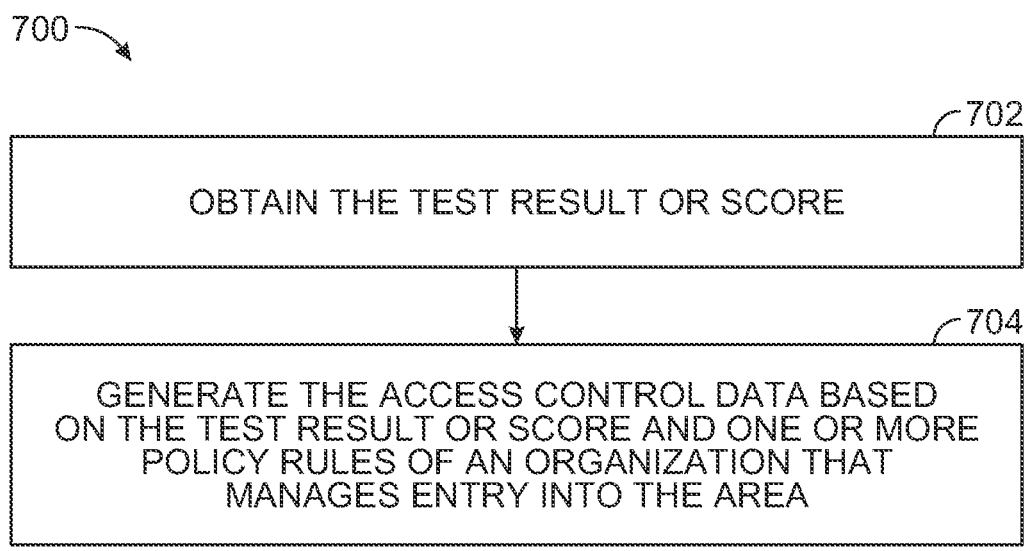
FIG. 7 is a flowchart for describing a method for access control for maintaining acceptable health and safety standards in group settings according to some embodiments, which also may be performed by the controller of the access control system and involve generating access control data based on a test result or score of a test of the user.

FIG. 7 is a flowchart for describing a method 700 for access control for maintaining acceptable health and safety standards in group settings according to some embodiments. In some embodiments, method 700 shown in FIG. 7 may be performed by a server (e.g. server 116 of FIGS. 1-3) which may interact with a controller of an access control system. In these embodiments, the one or more policy rules may be stored at the server or the controller. In an example embodiment, the server may be a local server in a private LAN or WLAN of an organization that manages entry into an area. In another example embodiment, the server may be an external server that is external to the private LAN or WLAN of the organization that manages entry. In other embodiments, method 700 shown in FIG. 7 may be performed by the user device of the user. In these other embodiments, the one or more policy rules may be stored at the user device. In any of the above-described embodiments, method 700 of FIG. 7 may be embodied in a computer program product having a non-transitory computer readable medium and instructions stored in the non-transitory computer readable medium, where the instructions are executable by one or more processors to perform steps of method 700.

In this embodiment, method 700 begins with a step 702. At step 702, the server or the device may obtain a test result or score of a test for assessing a risk of a user of having or developing a contagious illness. Next, method 700 may proceed to a step 704, where the server or the device may generate access control data based on the test result or score and one or more policy rules of an organization.

In Tables 1 and 2 below, two examples of policy tables for access control associated with the method of FIG. 7 are provided. In Table 1, access control data is determined according to a set policy rules according to the table. Here, a test result of a test may be one of positive, negative, or indeterminate. Per the policy rules (e.g. see Table 1), access control data for denying entry may be determined based on a positive test result and access control data for permitting entry may be determined based on a negative test result. In addition, access control data for permitting entry with a warning to re-test may be determined based on an indeterminate result when the user is identified as not been previously infected. On the other hand, access control data for denying entry until a re-test may be determined based on an indeterminate result when the user is identified as having been previously infected

TABLE 1

Policy Table for Access Control (Example 1)

| Test Result | | | Infection Assessment | Action for Access Control (Based on Policy Rules) |
|---|---|---|---|---|
| + | − | ? | | |
| 1 | 0 | 0 | Infected | Deny |
| 0 | 1 | 0 | Not Infected | Permit |
| 0 | 0 | 1 | Unknown | Permit or Depends* |

*If previously not infected, permit access with warning to re-test; if previously infected, deny access until re-test.

In Table 2, access control data is determined according to another set policy rules. Here again, a test result may be one of positive, negative, or indeterminate. However, an expiration period is set in order to expire old test result data, where re-testing is mandated. In addition, a grace period is offered for users who have expired test result data. This set of policy rules is explained in detail in the table for setting forth appropriate permissions and denials of entry.

TABLE 2

Policy Table for Access Control (Example 2)

| Test Result | | | Test Result Expiration? Within Grace Period | Test Result Expiration? Outside of Grace Period | Infection Assessment | Action for Access Control (Based on Policy Rules) |
|---|---|---|---|---|---|---|
| + | − | ? | | | | |
| 1 | 0 | 0 | x | x | Infected | Deny |
| 0 | 1 | 0 | 0 | 0 | Not Infected | Permit |

TABLE 2-continued

Policy Table for Access Control (Example 2)

| Test Result + | Test Result − | Test Result ? | Test Result Expiration? Within Grace Period | Test Result Expiration? Outside of Grace Period | Infection Assessment | Action for Access Control (Based on Policy Rules) |
|---|---|---|---|---|---|---|
| 0 | 1 | 0 | 1 | 0 | Likely Not Infected | Permit w/Warning |
| 0 | 1 | 0 | 0 | 1 | Unknown | Deny |
| 0 | 0 | 1 | 0 | 0 | Unknown | Permit or Depends* |
| 0 | 0 | 1 | 1 | 0 | Unknown | Permit or Depends* |
| 0 | 0 | 1 | 0 | 1 | Unknown | Deny |

*If previously not infected, permit with warning to re-test; if previously infected, deny access until re-test.

In some embodiments, other sets of policy rules may be similarly established for multiple findings (e.g. from antibody tests) or test scores, rather than for merely positive or negative test results (e.g. from viral tests).

Figure 8:
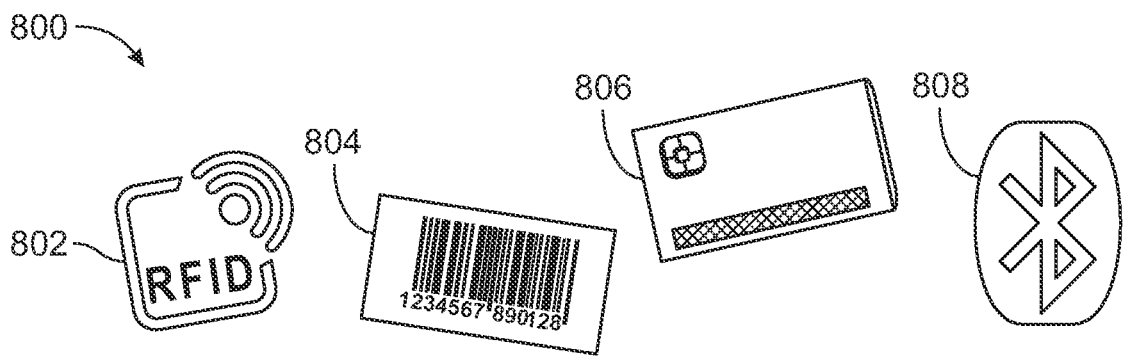
FIG. 8 is an illustration of a variety of different types of devices which may be utilized as or by the user device of the user.

As described above, in some embodiments, the user device may be an ID or access badge or device associated with the user. With reference now to FIG. 8, an illustrative representation of a variety of different types of devices 800 which may be utilized as, with, or in a user device for access control are shown, in accordance with various embodiments. In FIG. 8, devices 800 may include a Radio Frequency Identification (RFID) tag or device 802, an access card 804 having a bar code, a magnetic swipe card 806 which may also be a smart card, and a Bluetooth device 808 (e.g. based on IEEE 802.15) which may be included in a mobile user device or a stand-alone peripheral device, to illustrate but a few.

Thus, a variety of different types of devices may be utilized as, with, or in the user device associated with the user. Accordingly, magnetic or "swipe" cards for swipe card access systems may be utilized, proximity cards for proximity card access systems may be utilized (e.g. using 125 KHz proximity technology), smart cards for system card access systems may be utilized (e.g. using 13.56 KHz proximity technology), QR codes for QR code-based access systems, and so on. Swipe card access systems may utilize magnetic cards for basic, low security access control. Proximity cards may include printable PVC cards, clamshell cards, and others. Smart card access systems may provide more security and utilize contactless smart card technology to provide identification, authentication, and storage of information on the card (e.g. where the card includes a microchip and memory).

Figure 9:
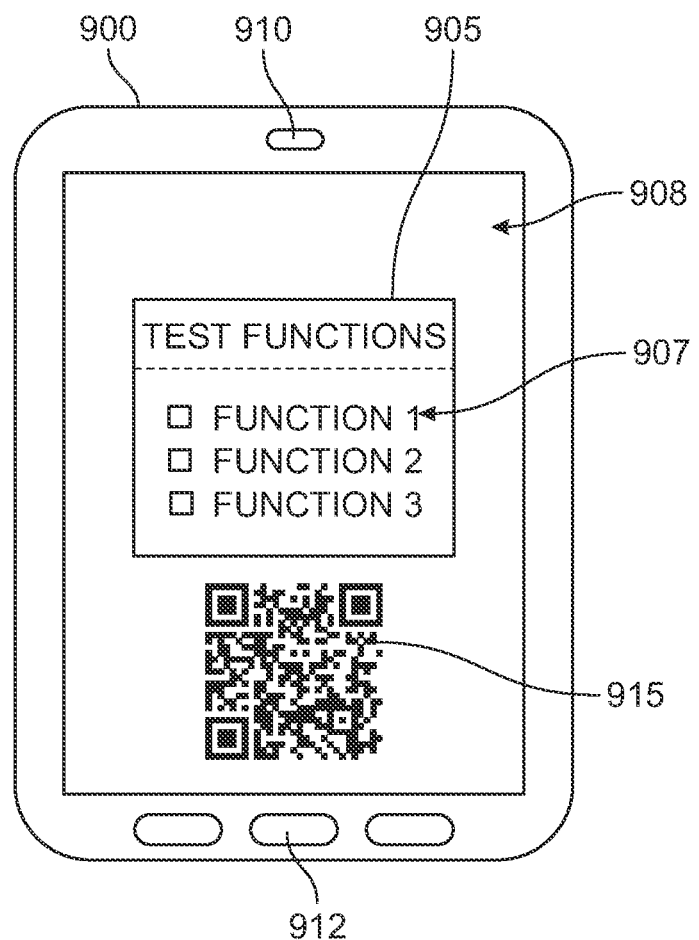
FIG. 9 is an illustration of a user device which is one type of a mobile user device which may have one or more test functions or illness risk factor assessment functions according to some embodiments.

FIG. 9 is an illustration of one type of a user device which, in this embodiment, is a mobile user device 900. In particular, mobile user device 900 of FIG. 9 is shown to be a (e.g. handheld) smartphone or a tablet computer. In FIG. 9, mobile user device 900 includes a user interface which may include a touch screen display 908, a speaker 910 and a microphone 912. In some embodiments, mobile user device 900 may include an application 905 having test functions 907 for a test for assessing a risk of the user of having or developing a contagious illness. The test functions 907 may be illness risk factor assessment functions, which may alternatively be referred to as symptom detection functions.

In some embodiments, as illustrated in FIG. 9, mobile user device 900 may cause QR code data 915 for access control to be displayed in the touch screen display. QR code data 915 for access control may be derived based on a test result or score of a test for the user, and may be displayed for being read by a reader of an access control system (see e.g. FIGS. 1-3). Thus, the display or touch screen display of mobile user device 900 for displaying QR code data may be used for access control.

Figure 10:
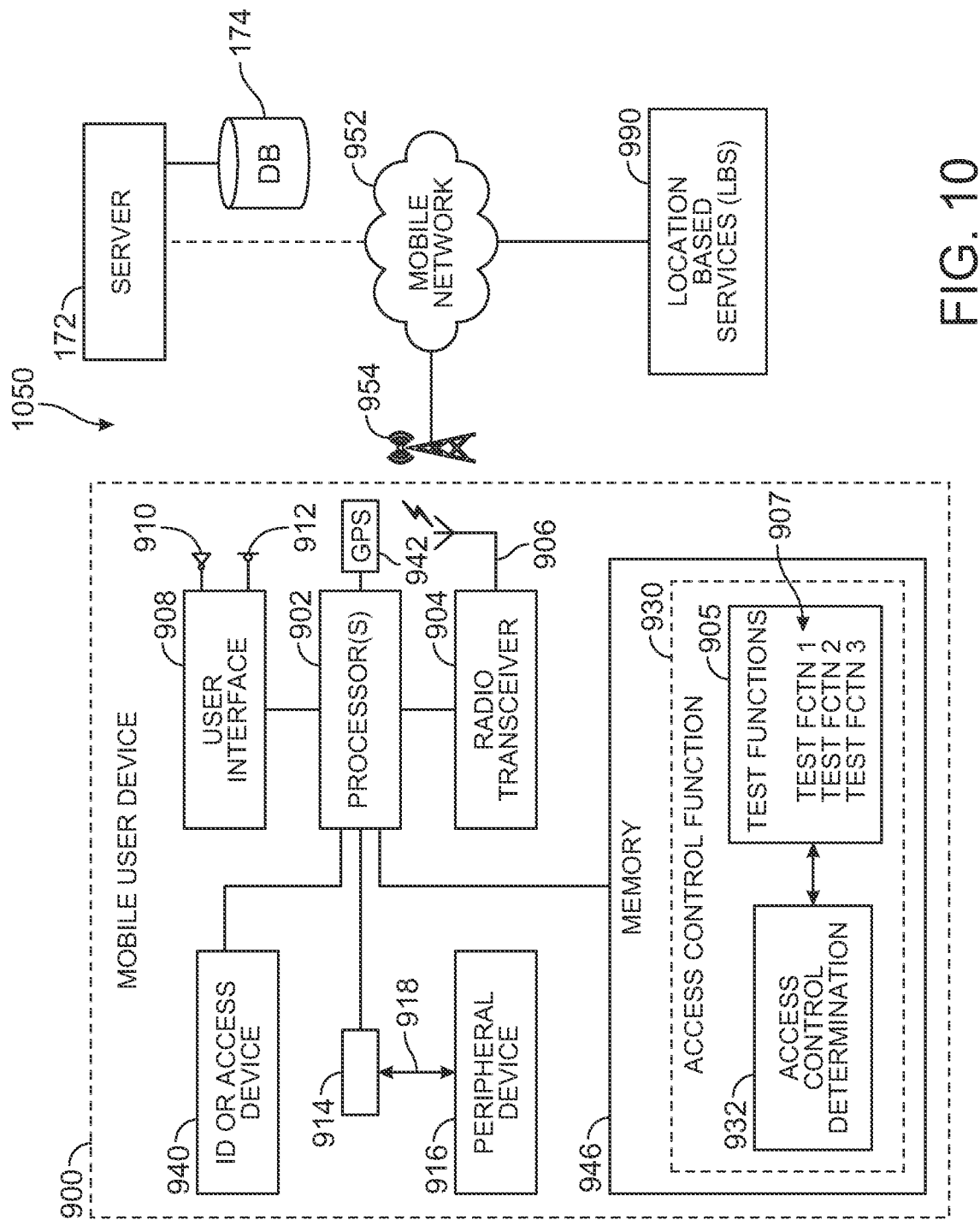
FIG. 10 is a schematic block diagram of a mobile user device which may connect in a mobile network for communications according to some embodiments.

FIG. 10 is a schematic block diagram of a mobile user device 900 which may connect in a mobile network 952 for communications according to some embodiments. Mobile user device 900 may include one or more processors 902, a memory 946, and a radio transceiver 904 with an antenna 906. Mobile user device 900 may also include user interface 908, speaker 910, and microphone 912 as previously identified in relation to FIG. 9. Radio transceiver 904 is configured to connect with mobile network 952 via a base station 954 to provide mobile user device 900 with mobile communications. In some embodiments, mobile user device 900 may include a peripheral interface for connecting a peripheral device 916 to mobile user device 900 via a connection or connector 918. With use of a global positioning system (GPS) device 942 of mobile user device 900, one or more servers 990 for location-based services (LBS) servers 990 in mobile network 952 may operate to provide location services for mobile user device 900.

Memory 946 may include an application 930 having an access control function for access control. One or more processors 902 may operate to execute applications of mobile user device 900, including application 930 for access control. Application 930 for access control may include or interact with application 905 having the test functions for the test for assessing the risk of the user of having or developing the contagious illness. The test functions of application 905 may be illness risk factor assessment functions, which may alternatively be referred to as symptom detection functions.

Figure 11:
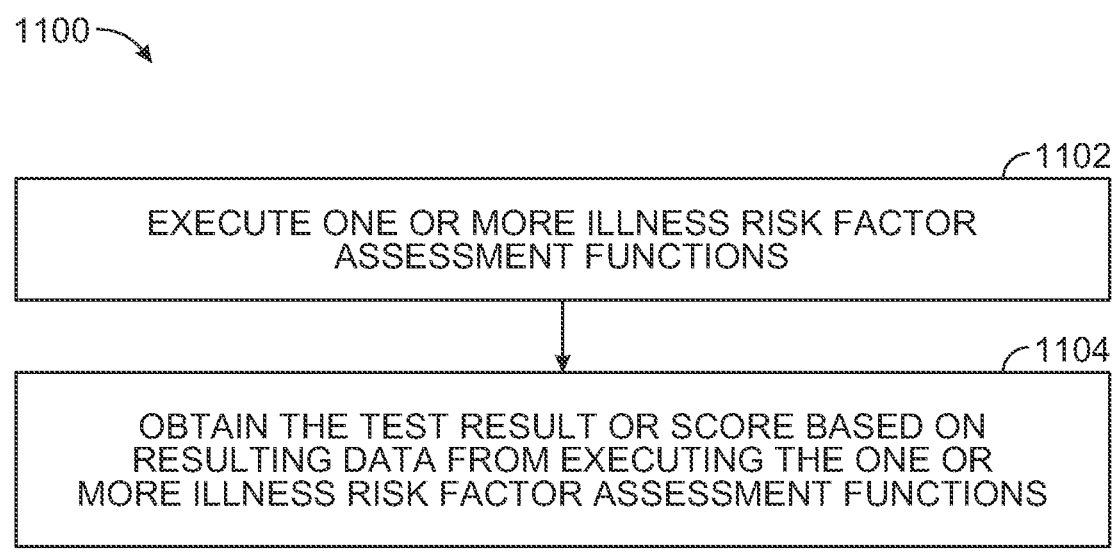
FIG. 11 is a flowchart for describing a method for obtaining a test result or score based on resulting data from executing the one or more illness risk factor assessment functions of the mobile user device according to some embodiments.

FIG. 11 is a flowchart for describing a method 1100 for obtaining a test result or score based on resulting data from executing one or more illness risk factor assessment functions according to some embodiments. In some embodiments, method 1100 shown in FIG. 11 may be performed by a mobile user device (e.g. the mobile user device 900 of FIGS. 9-10). In some cases, in particular, method 1100 shown in FIG. 11 may be performed by one or more processors of the mobile user device. In these embodiments, the mobile user device may have an application which includes one or more illness risk factor assessment functions which form all or part a test for assessing a risk of the user of having or developing a contagious illness. As described earlier, the illness risk factor assessment functions may alternatively be referred to as symptom detection functions.

In this embodiment, method 1100 begins with a step 1102. At step 1102, the one or more illness risk factor assessment functions of the mobile user device may be executed. In one example, each one of the one or more illness risk factor assessment functions of the mobile user device may be executed in a serial manner with assistance of the user. Next, method 1100 may proceed to a step 1104, where the test result or score of the test may be obtained based on resulting data from executing the one or more illness risk factor assessment functions.

In some embodiments of method 1100, at step 1104, the test result or score of the test may be obtained based on combining the resulting data from each one of the one or more illness risk factor assessment functions. For example, the resulting data from each one of the one or more illness risk factor assessment functions may be combined or averaged. The access control data may then be derived, determined or retrieved based on the test result or score of the test.

At least some of the one or more illness risk factor assessment functions may be utilized to identify or detect a symptom of the user at the mobile user device 900. A user having a contagious illness may have a range of different symptoms, ranging from mild to severe. For example, individuals with COVID-19 are associated with a wide range of different symptoms, from mild to severe, which surface after a period of time after exposure to the virus (e.g. 2-14 days). Symptoms associated with COVID-19 may include a cough, a shortness of breath or difficulty breathing, a fever, chills, a sore throat, a new loss of taste or smell, muscle pain, as well as other symptoms.

In some embodiments of method 1100 of FIG. 11, the one or more illness risk factor assessment functions provided at the mobile user device may include a temperature detection function which is based on a temperature of the user; an image-based symptom recognition function which is based on facial characteristics of the user, using a camera of the mobile user device; an audio-based symptom recognition function which is based on qualities of voice, nasal, or congestion of the user, using an audio recorder of the mobile user device; or a pulse oximeter function which is based on a blood oxygenation of the user.

Figure 12:
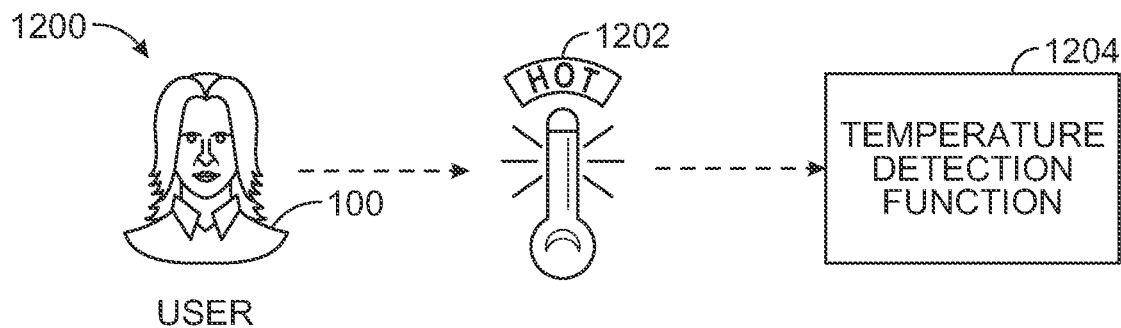
FIG. 12 is an illustrative scenario of the use of a temperature detection function which may be executed by the mobile user device.
Figure 13:
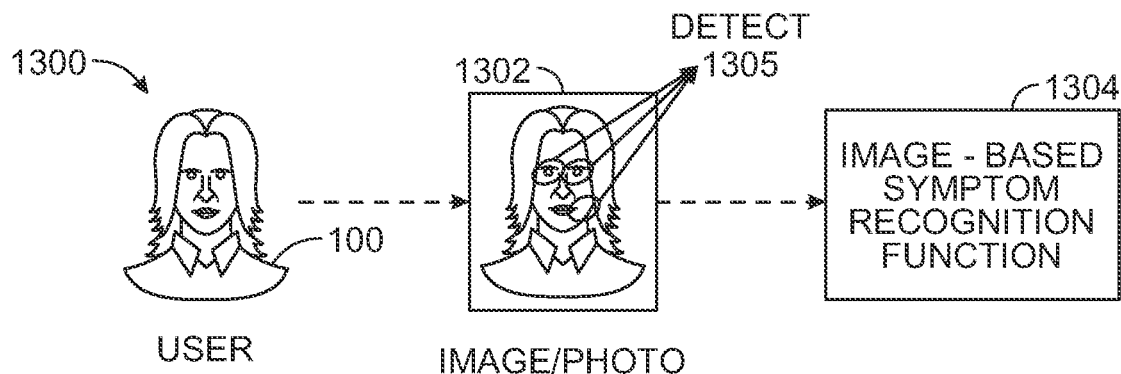
FIG. 13 is an illustrative scenario of the use of an image-based symptom recognition function which may be executed by the mobile user device.
Figure 14:
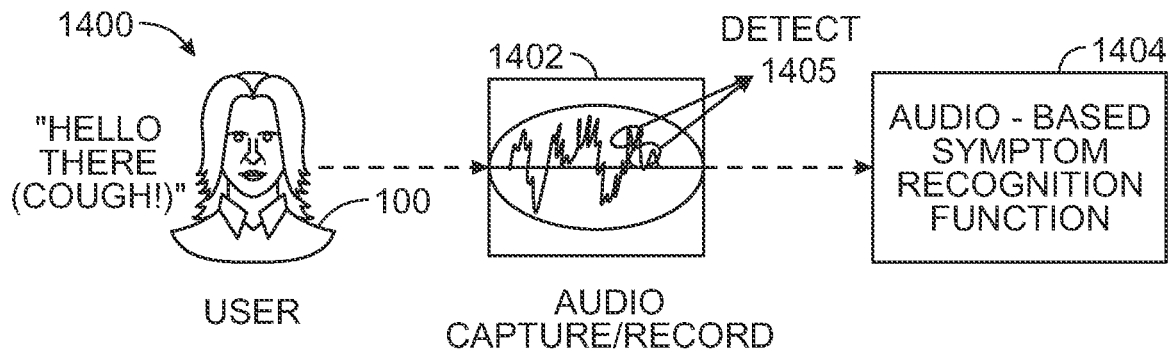
FIG. 14 is an illustrative scenario of the use of an audio-based symptom recognition function which may be executed by the mobile user device.

To better illustrate the techniques of the present embodiments, FIGS. 12-14 are illustrative scenarios of the use of various illness risk factor assessment functions of the mobile user device, according to example embodiments.

Beginning with FIG. 12, an illustrative scenario 1200 of the use of a temperature detection function 1204 of the mobile user device is shown. Temperature detection function 1204 operates to obtain a temperature reading 1202 of user 100 and determine, based on temperature reading 1202, a score corresponding to an illness risk factor for assessing the risk of user 100 of having or developing the contagious illness. In some embodiments, temperature detection function 1204 may be executed with use of an electronic thermometer or other sensor for reading the temperature of user 100. In some embodiments, an electronic thermometer or other sensor may be connected to the mobile user device as a peripheral device (see e.g. peripheral device 916 having connection 918 with mobile user device 900). In other embodiments, a fingerprint thermometer may be provided with use of a fingerprint scanner of the mobile user device; the fingerprint scanner may be the existing, built-in fingerprint scanner of the mobile user device.

In FIG. 13, an illustrative scenario 1300 of the use of an image-based symptom recognition function 1304 of the mobile user device is shown. Image-based symptom recognition function 1304 may be for detecting symptoms of the contagious illness based on facial characteristics of the user. Image-based symptom recognition function 1304 of the mobile user device may be executed with use of a camera of the mobile user device. In one example, the camera is the existing, built-in camera of the mobile user device. Here, image-based symptom recognition function 1304 may cause an image or photo 1302 of the face of user 100 to be captured, and identify or detect one or more symptomatic features 1302 associated with the contagious illness based on the image or photo 1302. Image-based symptom recognition function 1304 may then determine, based on the one or more symptomatic features 1302, a score corresponding to an illness risk factor for assessing the risk of the user of having or developing the contagious illness.

In FIG. 14, an illustrative scenario 1400 of the use of an audio-based symptom recognition function 1404 of the mobile user device is shown. Audio-based symptom recognition function 1404 may be for detecting symptoms of the contagious illness based on audio qualities, i.e. qualities of voice, nasal, or congestion of user 100. Audio-based symptom recognition function 1404 of the mobile user device may be executed with use of an audio recorder of the mobile user device. In one example, the audio recorder may be the existing, built-in audio recorder of the mobile user device. Here, audio-based symptom recognition function 1404 may cause an audio clip 1402 of user 100 to be captured (e.g. where user 100 is speaking into the mobile user device), and then identify or detect one or more symptomatic features 1405 associated with the contagious illness based on audio clip 1402. Audio-based symptom recognition function 1404 may then determine, based on the one or more symptomatic features 1402, a score corresponding to an illness risk factor for assessing the risk of the user of having or developing the contagious illness.

In an example embodiment, the pulse oximeter function of the mobile user device may be configured to measure the proportion of oxygenated hemoglobin in the blood in pulsating vessels, especially the capillaries of the finger or ear. In particular, the pulse oximeter function may determine a heart rate and a peripheral capillary oxygen saturation (SpO2) of the user. The pulse oximeter function may determine, based on the heart rate and/or SpO2, a score corresponding to an illness risk factor for assessing the risk of the user of having or developing the contagious illness. For measurements, the pulse oximeter function may prompt the user to place his or her finer over the camera and lens while measurements are taken.

Notably, in some embodiments, the test result or score may be based on an actual "lab" test for the contagious illness (e.g. COVID-19). Currently, there are two kinds of tests available for COVID-19: a viral test and an antibody test. A viral test may indicate if you currently have an infection with SARS-CoV-2, the virus that causes COVID-19. Molecular and antigen tests are types of viral tests, which may also be referred to as diagnostic tests. An antibody test may indicate if an individual has previously had an infection with SARS-CoV-2. This type of test may also be referred to as a serological test. In one example, a test kit may be provided for detecting a presence or absence of ribonucleic acid (RNA) material from a virus (e.g. SARS-CoV-2). The test kit may be in the form of an at-home test kit. Different types of authorized at-home test kits are commercially available from several different reputable companies.

If the test result of a viral test is positive for COVID-19, the individual should be informed of protective measures to take, especially if the individual is noticeably sick or has symptoms, or caring for someone else. If the test result of the viral test is negative for COVID-19, the individual was (likely) not infected at the time the sample was collected. However, that does not necessary mean that the individual will not get sick. The test result only means that the individual did not have COVID-19 at the time of testing. The individual might test negative if the sample was collected early in the infection but then test positive later on.

On the other hand, an antibody test may indicate if an individual has previously had SARS-CoV-2. The antibody test may be processed in a health care laboratory. In one example, the antibody test may test for an antibody referred to as immunoglobulin G (IgG) to indicate if an individual has previously had SARS-CoV-2. In this example, test results of the antibody test may correspond to one of four different findings: Pending, Not Detected, Borderline, or Detected. In a finding of "Pending," the health care laboratory may still be processing a blood sample of an individual. In a finding of "Not Detected" (or "negative"), IgG antibodies to SARS-CoV-2 were not detected in the blood of the individual. Note that a negative result for IgG antibodies does not rule out a SARS-CoV-2 infection, particularly for individuals who have been in contact with the virus (e.g. the individual's immune function may have been suppressed by other health issues or the antibody level is too low for the test to detect). In a finding of "Borderline," IgG antibodies to SARS-CoV-2 were detected, but at a level that was too low to determine whether the individual has had a past infection. Note that a borderline result may indicate a very early infection or a prior infection with one or more other coronaviruses. In a finding of "Detected," IgG antibodies to SARS-CoV-2 were detected in the blood of the individual at a level that was sufficient to determine that the individual has had a past infection with SARS-CoV-2.

Figure 15:
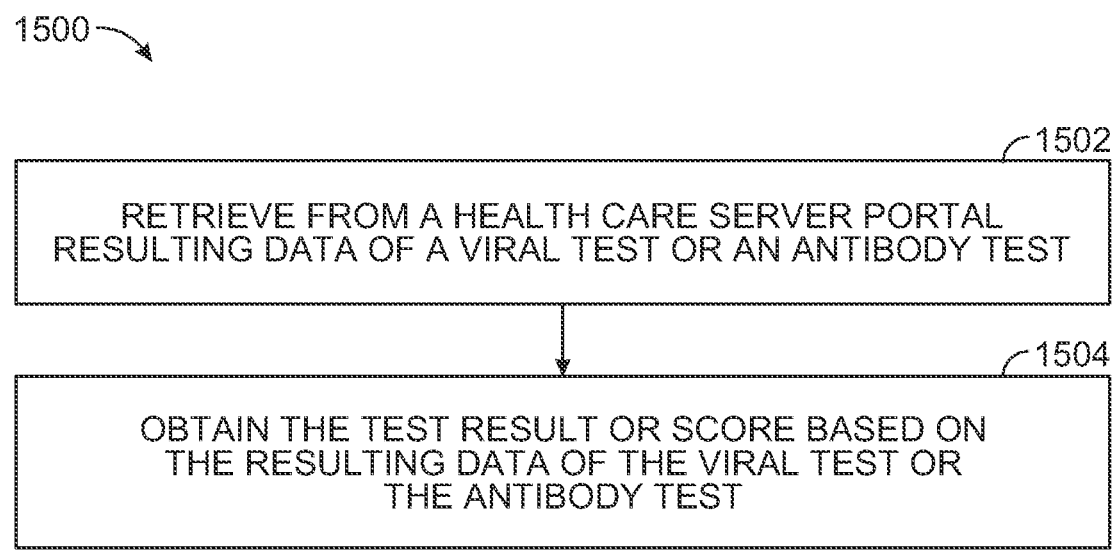
FIG. 15 is a flowchart for describing a method for obtaining a test result or score based on resulting data of a viral test or an antibody test obtained from a health care server portal by the mobile user device according to some embodiments.

FIG. 15 is a flowchart for describing a method 1500 for obtaining a test result or score based on resulting data of a viral test or an antibody test according to some embodiments. A viral test or an antibody test for a user may be processed at a health care laboratory based on a sample of the user (e.g. a swab from the nose or the throat of the user, a blood sample of the user, etc.). Resulting data of the viral test or the antibody test may be generated based on the sample. The resulting data may be provided in the form of electronic data which is made privately available for viewing or retrieval via a health care server portal.

In this embodiment, method 1500 begins with a step 1502. At step 1502, the mobile user device may retrieve, from the health care server portal, the resulting data of the viral test or the antibody test of the user. Next, method 1500 may proceed to a step 1504, where the test result or score of the test may be obtained based on the resulting data of the viral test or the antibody test.

In one example of method 1500, at step 1504, the resulting data of the viral test or the antibody test is the test result or score. In another example of method 1500, at step 1504, the test result or score of the test may be obtained based on the resulting data of the viral test or the antibody test, as well as resulting data from executing the one or more illness risk factor assessment functions (see e.g. the above description associated with FIGS. 11-14). The access control data may then be derived, determined or retrieved based on the test result or score of the test.

Figure 16:
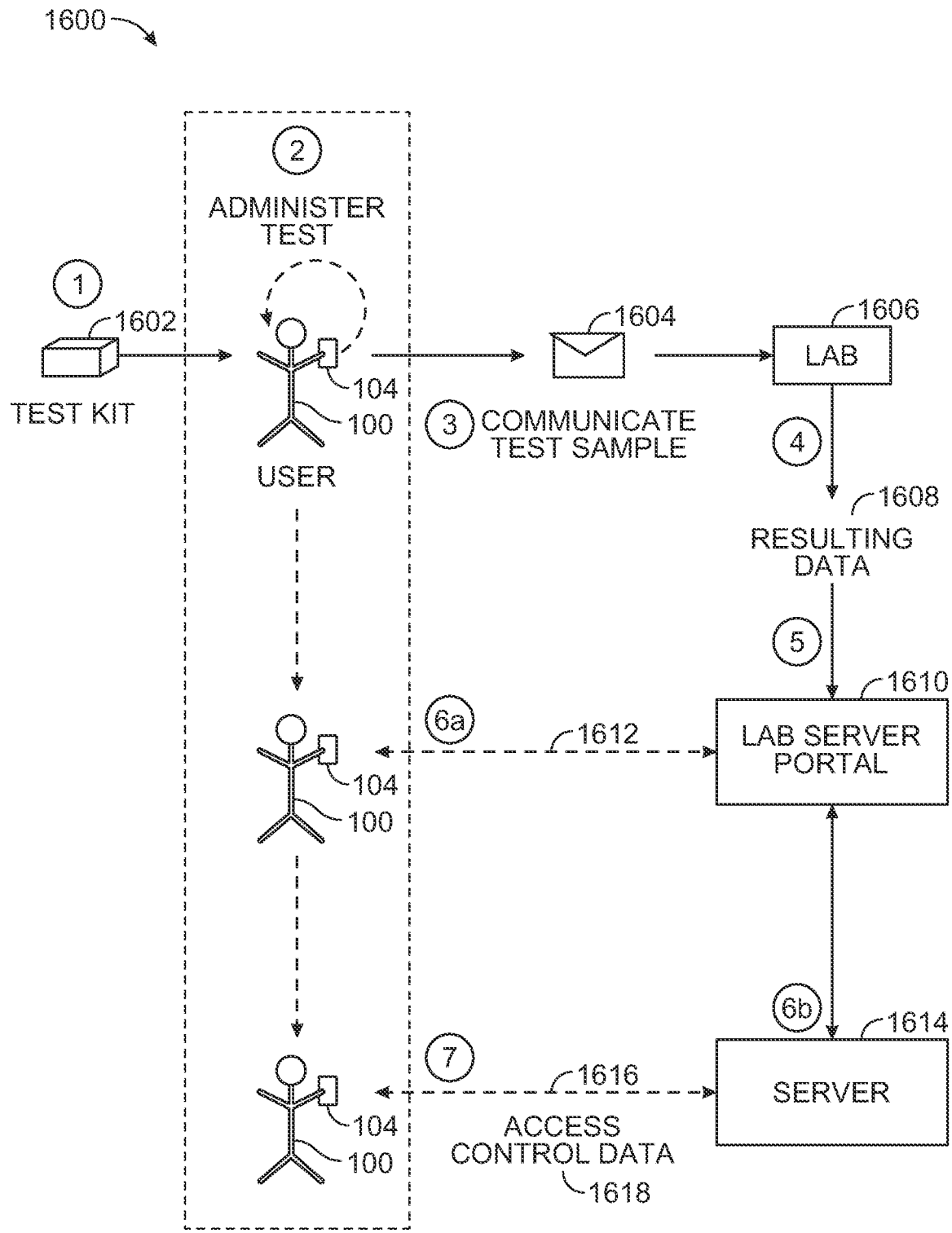
FIG. 16 is a process flow diagram of a process flow for obtaining a test result or score based on resulting data of a viral test or an antibody test obtained from a health care server portal by the mobile user device according to some embodiments.

FIG. 16 is a process flow diagram of a process flow 1600 for obtaining a test result or score based on resulting data of a viral test or an antibody test according to some embodiments. In this embodiment, process flow 1600 begins with a step 1. At step 1, a test for assessing a risk of a user of having or developing a contagious illness is obtained. In this example, the test is in the form of a test kit 1602 and, in particular, test kit 1602 may be an at-home test kit. The test may be for a viral test or an antibody test for the contagious illness. Next, process flow 1600 may proceed to a step 2, where the test is administered (e.g. at home or at employer) using the test kit to produce a test sample (e.g. a swab from the nose or the throat of the user, a blood sample of the user, etc.). Next, process flow 1600 may proceed to a step 3, where user 100 may then communicate or send the sample to a health care laboratory or "lab" 1606 via a package or mailing 1604. The viral test or the antibody test for the user may be processed at the health care laboratory 1606 based on the sample of user 100.

Next, process flow 1600 may proceed to a step 4, where resulting data 1608 of the viral test or the antibody test may be generated based on the sample. Next, process flow 1600 may proceed to a step 5, where the resulting data 1610 may be provided in the form of electronic data which is made privately available for viewing or retrieval via a health care server portal 1610 (or "lab server portal"). Next, process flow 1600 may proceed to a step 6a, where user device 104 (e.g. a mobile user device) may retrieve or obtain the resulting data from the health care server portal 1610 in a communication 1612 (e.g. securely and privately via authentication). In some cases, the resulting data may be viewed at user device 104.

In some embodiments of step 6a of process flow 1600, user device 104 or its application may automatically retrieve or obtain the resulting data that is captured in the application (e.g. for providing access control). In some cases, user device 104 may retrieve the resulting data by regularly or periodically checking health care server portal 1610 for the resulting data. In other cases, health care server portal 1610 may send to user device 104 a notification in response to availability of the resulting data and, in response, user device 104 may then automatically retrieve or obtain the resulting data that is captured in the application.

In some embodiments of process flow 1600, after step 6a, user device 104 may derive or determine access control data based on the resulting data received from health care server portal 1610.

In other embodiments of process flow 1600, after step 6a, alternative steps 6b and 7 may be carried out. Process flow 1600 may proceed to a step 6b, where a server 1614 (e.g. a trusted server) may retrieve or obtain the resulting data of user 100 from health care server portal 1610 (e.g. securely and privately via authentication). In an example embodiment, server 1614 may be a local server in a private LAN or WLAN of an organization that manages entry into an area. In another example embodiment, server 1614 may be an external server that is external to the private LAN or WLAN of the organization that manages entry. In some cases, server 1614 may be server 116 described in relation to FIGS. 1-3.

In an example embodiment of step 6b of process flow 1600, server 1614 may automatically retrieve or obtain the resulting data associated with user 100. In some cases, server 1614 may retrieve the resulting data by regularly or periodically checking health care server portal 1610 for the resulting data. In another example embodiment of step 6b of process flow 1600, health care server portal 1610 may send to server 1614 a notification in response to availability of the resulting data and, in response, server 1614 may then automatically retrieve or obtain the resulting data.

Server 1614 may be configured to derive or determine access control data for user 100 (as well as other users) based on the resulting data. Next, process flow 1600 may proceed to step 7, where user device 104 (e.g. the mobile user device) may retrieve or obtain access control data 1618 from server 1614 in a communication 1616. In an example embodiment of step 7 of process flow 1600, user device 104 or its application may automatically retrieve or obtain the access control data 1618 that is captured in the application (e.g. for providing access control). Here, user device 104 may retrieve the access control data 1618 by regularly or periodically checking server 1614 for the resulting data. In another example embodiment of step 7 of process flow 1600, server 1614 may send to user device 104 a notification in response to availability of the access control data 1618 and, in response, user device 104 may then automatically retrieve or obtain the access control data 1618 that is captured in the application (e.g. for providing access control).

In some embodiments of step 7 of process flow 1600, access control data 1618 from server 1614 may be QR code data for access control for display in the display or touch screen display of user device 104. For example, as described above in reference to FIG. 9.

Accordingly, techniques and mechanisms of the present disclosure may provide reasonable measures to prevent the spread of disease in operating environments (e.g. employment environments). Assurance of health and safety in group settings are easily facilitated, leveraging existing technology where possible to minimize changes to existing devices, systems, and network architectures. By excluding actual test results or scores of the tests of the users in the access control methodologies, compliance with HIPAA and/or other regulatory standards, policies, and practices may be established. Use of sensitive test results or scores of users in the network or system may be immediately discarded (e.g. deleted or cleared) after derivation of access control data.

The processes and methods of the embodiments described in this detailed description and shown in the figures can be implemented using any kind of servers or devices having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on servers or devices including read only memory (ROM) and/or random access memory (RAM), which may be connected to one or more processing units. Examples of servers and devices include, but are not limited to: enterprise servers, cloud servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. Examples of media that can be used for storage include erasable programmable read-only memory (EPROM), electrically erasable programmable read-only memories (EEPROM), solid state drives, magnetic disks or tapes, optical disks, CD ROM disks and DVD-ROM disks.

The embodiments may utilize any kind of network for communication between separate computing systems. A network can comprise any combination of LANs and/or WANs, using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (IPsec).

For each of the exemplary processes described above including multiple steps, it may be understood that other embodiments some steps may be omitted and/or reordered. In some other embodiments, additional steps could also be possible.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

The invention claimed is:

1. A method comprising:
at a user device,
obtaining access control data which is derived based on a test result or score of a test for assessing a risk of a user of having or developing a contagious illness;
executing an illness risk factor assessment function on the user device which comprises the test, wherein the illness risk factor assessment function is an image-based symptom recognition function which is based on facial characteristics of the user obtained through a camera of the user device;
obtaining the test result or score based on resulting data from executing the illness risk factor assessment function; and
communicating the access control data to an access control system in response to a reading of the user device by the access control system, for causing the access control system to permit or deny entry of the user into an area.

2. The method of claim 1,
wherein obtaining the test result or score of the test based on the resulting data from executing the illness risk factor assessment function comprises detecting one or more symptomatic features associated with the contagious illness from the facial characteristics of the user obtained through the camera of the user device.

3. The method of claim 1, further comprising:
at the user device,
executing at least one additional illness risk factor assessment function which comprises the test; and
obtaining the test result or score based on resulting data from executing the at least one additional illness risk factor assessment function.

4. The method of claim 3, wherein the at least one additional illness risk factor assessment function comprises one or more of:
a temperature detection function which is based on a temperature of the user;
or
an audio-based symptom recognition function which is based on qualities of voice, nasal, or congestion of the user.

5. The method of claim 4, wherein the at least one additional illness risk factor assessment function comprises a pulse oximeter function which is based on a blood oxygenation of the user.

6. The method of claim 1, wherein obtaining the access control data further comprises:
at the user device,
retrieving from a server the access control data which is derived based on the test result or score of the test.

7. The method of claim 1, wherein the test further comprises a viral test or an antibody test, and wherein obtaining the access control data further comprises:
- at the user device comprising a mobile user device,
  - retrieving from a health care server portal the test result or score of the test comprising the viral test or the antibody test.

8. The method of claim 1, further comprising:
- at the user device comprising a mobile user device,
  - retrieving from a server the access control data which is derived based on the test result or score of the test,
  - wherein the access control data comprises QR code data for display for the reading of the user device by the access control system.

9. The method of claim 1, wherein the user device comprises an application executing on a processor of the user device, the application including the illness risk factor assessment function.

10. The method of claim 1, wherein the user device comprises a mobile user device which is one of a smartphone or a tablet computer.

11. A mobile user device comprising:
- one or more processors;
- a user interface comprising a touch screen display;
- a radio transceiver configured to connect to a mobile network for communications; and
- a camera;
- the one or more processors configured to:
  - obtain access control data which is derived based on a test result or score of a test for assessing a risk of a user of having or developing a contagious illness;
  - execute an illness risk factor assessment function on the mobile user device which comprises the test, wherein the illness risk factor assessment function is an image-based symptom recognition function which is based on facial characteristics of the user obtained through the camera of the mobile user device;
  - obtain the test result or score based on resulting data from executing the illness risk factor assessment function; and
  - communicate the access control data to an access control system in response to a reading of the mobile user device by the access control system, for causing the access control system to permit or deny entry of the user into an area.

12. The mobile user device of claim 11, wherein the test is further based on at least one additional illness risk factor assessment function performed by the mobile user device, the at least one additional illness risk factor assessment function comprising one or more of:
- a temperature detection function which is based on a temperature of the user;
- an audio-based symptom recognition function which is based on qualities of voice, nasal, or congestion of the user, using an audio recorder of the mobile user device, or
- a pulse oximeter function which is based on a blood oxygenation of the user.

13. The mobile user device of claim 11, wherein the one or more processors are further configured to:
- retrieve, from a health care server portal, resulting data of a viral test or an antibody test,
- wherein the test result or score of the test is further based on the resulting data of the viral test or the antibody test.

14. A method comprising:
- at a controller of an access control system,
  - obtaining access control data based on a reading of a user device of a user, the access control data being derived based on a test result or score of a test for assessing a risk of the user of having or developing a contagious illness;
  - wherein the user device is configured to execute an illness risk factor assessment function which comprises the test, wherein the illness risk factor assessment function is an image-based symptom recognition function which is based on facial characteristics of the user obtained through a camera of the user device;
  - wherein the user is device is further configured to obtain the test result or score based on resulting data from executing the illness risk factor assessment function;
  - communicating a signal to an entry mechanism of the access control system, for permitting or denying entry of the user into an area based on the access control data.

15. The method of claim 14, wherein obtaining the access control data based on the reading of the user device further comprises:
- obtaining from the user device the access control data.

16. The method of claim 14, wherein obtaining the access control data based on the reading of the user device further comprises:
- obtaining from the user device an identifier of the user; and
- retrieving from a server the access control data based on the identifier of the user.

17. The method of claim 16, wherein:
- the server comprises a local server in a local area network of an organization that manages entry into the area, or
- the server comprises an external server that is external to the local area network of the organization that manages entry into the area.

18. The method of claim 14, wherein obtaining the access control data further comprises:
- obtaining the test result or score; and
- generating the access control data based on the test result or score and one or more policy rules of an organization that manages entry into the area,
- wherein obtaining the test result or score further comprises:
  - obtaining the test result or score from the user device having one or more illness risk factor assessment functions which comprise the test, or
  - retrieving from a health care server portal the test result or score of the test comprising a viral test or an antibody test.

19. The method of claim 14, wherein the access control data has at least a first indication value and a second indication value, the first indication value being for permitting the entry based on the test result or score being a negative test result or being within a limit set by a threshold value, and the second indication value being for denying the entry based on the test result or score being a positive test result or being outside the limit set by the threshold value.

20. The method of claim 14, wherein the access control data comprises QR code data and the reading of the user device is performed with use of a QR code reader.

* * * * *